United States Patent
Ramani et al.

(10) Patent No.: US 10,543,361 B2
(45) Date of Patent: Jan. 28, 2020

(54) SYSTEM AND METHOD FOR LOCALIZATION OF DEEP BRAIN STIMULATION ELECTRODE VIA MAGNETIC RESONANCE IMAGING

(71) Applicant: General Electric Company, Schenectady, NY (US)

(72) Inventors: Sathish Ramani, Niskayuna, NY (US); Rolf Schulte, Bavaria (DE); Ileana Hancu, Clifton Park, NY (US); Jeffrey Ashe, Gloversville, NY (US); Graeme C. McKinnon, Hartland, WI (US)

(73) Assignee: General Electric Company, Schenectady, NY (US)

( * ) Notice: Subject to any disclaimer, the term of this patent is extended or adjusted under 35 U.S.C. 154(b) by 172 days.

(21) Appl. No.: 15/899,594

(22) Filed: Feb. 20, 2018

(65) Prior Publication Data

US 2019/0255315 A1 Aug. 22, 2019

(51) Int. Cl.
*A61B 5/055* (2006.01)
*A61N 1/05* (2006.01)
*A61N 1/36* (2006.01)

(52) U.S. Cl.
CPC ............ *A61N 1/0534* (2013.01); *A61B 5/055* (2013.01); *A61N 1/36082* (2013.01); *A61N 1/36067* (2013.01)

(58) Field of Classification Search
None
See application file for complete search history.

(56) References Cited

U.S. PATENT DOCUMENTS 7,979,129 B2 7/2011 Gill
8,369,931 B2 2/2013 Paek et al.
(Continued)

FOREIGN PATENT DOCUMENTS

| WO | 2014155203 A1 | 10/2014 |
|---|---|---|
| WO | 2016142675 A1 | 9/2016 |
| WO | 2017010930 A1 | 1/2017 |

OTHER PUBLICATIONS

Madio et al., "Ultra-Fast Imaging Using Low Flip Angles and FIDs", Magnetic Resonance in Medicine, vol. 34, No. 4, Oct. 1995, pp. 525-529.
(Continued)

*Primary Examiner* — Kennedy Schaetzle
(74) *Attorney, Agent, or Firm* — Ziolkowski Patent Solutions Group, SC; Jean K. Testa

(57) ABSTRACT

A system and method for localizing a deep brain stimulation electrode in vivo in a subject or object is provided. A magnetic resonance imaging system obtains MR image data from a volume-of-interest by way of a zero echo time (ZTE) or ultrashort echo time (UTE) pulse sequence, with one or more of a phase domain image and a magnitude domain image being analyzed from the MR image data acquired by the ZTE or UTE pulse sequence. One or more electrodes are localized within the volume-of-interest based on an analysis of the phase domain image and/or magnitude domain image. In localizing the electrodes, a multi-scale correlation-based analysis of the volume-of-interest is performed to estimate at least one of an electrode center and electrode contact locations of the electrode, with the localization being achieved with a fast scan-time and with a high level of accuracy and precision.

25 Claims, 10 Drawing Sheets

(56) References Cited

U.S. PATENT DOCUMENTS

| | | | |
|---|---|---|---|
| 9,220,458 | B2 | 12/2015 | Pouratian |
| 9,760,688 | B2 | 9/2017 | McIntyre et al. |
| 2007/0167856 | A1 | 7/2007 | McNames et al. |
| 2010/0114281 | A1 | 5/2010 | Swoyer et al. |
| 2010/0135559 | A1* | 6/2010 | Morich ............ G01R 33/481 382/131 |
| 2012/0116211 | A1 | 5/2012 | McIntyre et al. |
| 2015/0283379 | A1 | 10/2015 | Venkatesan |
| 2017/0056678 | A1 | 3/2017 | Bokil |

OTHER PUBLICATIONS

Marques et al., "Application of a Fourier-Based Method for Rapid Calculation of Field Inhomogeneity Due to Spatial Variation of Magnetic Susceptibility", Concepts in Magnetic Resonance, vol. 25B, No. 1, Apr. 13, 2005, pp. 65-78.

Pinsker et al., "Accuracy and Distortion of Deep Brain Stimulation Electrodes on Postoperative MRI and CT", Zentralbl Neurochir, vol. 69, No. 3, Aug. 2008, pp. 144-147.

Ellis et al., "Reoperation for Suboptimal Outcomes After Deep Brain Stimulation Surgery", Neurosurgery, vol. 63, No. 4, Oct. 2008, pp. 754-761.

Lee et al., "Is MRI a reliable tool to locate the electrode after deep brain stimulation surgery? Comparison study of CT and MRI for the localization of electrodes after DBS", Acta Neurochir, vol. 152, No. 12, Dec. 2010, pp. 2029-2036.

Carl et al., "Investigations of the Origin of Phase Differences Seen with Ultrashort TE Imaging of Short T2 Meniscal Tissue", Magnetic Resonance in Medicine, vol. 67, No. 4, Apr. 2012, pp. 991-1003.

Blomstedt et al., "Reoperation After Failed Deep Brain Stimulation for Essential Tremor", World Neurosurgery, vol. 78, No. 5, Nov. 2012, pp. 554.E1-554.E5.

Jeong et al., "Focused Current Density Imaging Using Internal Electrode in Magnetic Resonance Electrical Impedance Tomography (MREIT)", IEEE Transactions on Biomedical Engineering, vol. 61, No. 7, Jul. 2014, pp. 1938-1946.

Shukla et al., "State of the Art for Deep Brain Stimulation Therapy in Movement Disorders: A Clinical and Technological Perspective", IEEE Reviews in Biomedical Engineering, vol. 9, 2016, pp. 219-233.

* cited by examiner

|  |  | MEAN POSITION DIFFERENCE [mm] | STANDARD DEVIATION OF POSITION DIFFERENCE [mm] | MINIMUM POSITION DIFFERENCE [mm] | MAXIMUM POSITION DIFFERENCE [mm] |
|---|---|---|---|---|---|
| CONTACT 1 | SPGR TO CT | 0.46 | 0.28 | 0.09 | 0.98 |
| | ZTE[phase] TO CT | 0.31 | 0.11 | 0.15 | 0.54 |
| CONTACT 2 | SPGR TO CT | 0.54 | 0.32 | 0.16 | 1.13 |
| | ZTE[phase] TO CT | 0.30 | 0.09 | 0.09 | 0.49 |
| CONTACT 3 | SPGR TO CT | 0.67 | 0.31 | 0.26 | 1.25 |
| | ZTE[phase] TO CT | 0.31 | 0.09 | 0.13 | 0.52 |
| CONTACT 4 | SPGR TO CT | 0.70 | 0.26 | 0.32 | 1.28 |
| | ZTE[phase] TO CT | 0.36 | 0.11 | 0.19 | 0.61 |
| ELECTRODE CENTER | SPGR TO CT | 0.69 | 0.45 | 0.11 | 1.49 |
| | ZTE[phase] TO CT | 0.32 | 0.09 | 0.14 | 0.52 |

FIG. 13

SYSTEM AND METHOD FOR LOCALIZATION OF DEEP BRAIN STIMULATION ELECTRODE VIA MAGNETIC RESONANCE IMAGING

BACKGROUND OF THE INVENTION

Embodiments of the invention relate generally to a deep brain stimulation (DBS), and more particularly to a system and method for improving localization of an implanted DBS electrode via the use of a zero or ultra-short echo time (ZTE/UTE) magnetic resonance (MR) imaging technique.

Deep brain stimulation (DBS) is a well-established approach for treating disabling neurological symptoms and psychiatric disorders. The procedure uses a neurostimulator to deliver electrical stimulation to the brain by way of surgically implanted electrodes. Depending on the condition being treated, the electrodes can be used to target certain cells and chemicals within the brain or to target areas of the brain that control movement or regulate abnormal impulses. In this later case, the electrical stimulation can be used to disrupt abnormal nerve signals that cause tremor and other neurological symptoms. Over the past 20 years, more than 50,000 Parkinson's disease, essential tremor, dystonia and obsessive-compulsive disorder patients have seen significant symptom relief due to DBS treatment. Evidence now accumulates indicating that patients with chronic pain, post-traumatic stress disorder, and obesity may also benefit from DBS treatments.

In employing DBS treatments, locating the DBS electrode post-operatively is important for assessing surgery success in accurately implanting the electrode and for subsequently aiding device programming (i.e., selecting one or more electrodes from an array of electrodes for delivering electrical stimulation to the brain of a patient), with it being recognized that differences between an intended electrode target location and the actual electrode implantation location larger than 2 mm can result in a suboptimal outcome and may require reoperation. Post-operative locating of the DBS electrode is presently done via a performing of a post-implantation imaging technique—with computed tomography (CT) imaging or magnetic resonance (MR) imaging that utilizes a known long-readout technique (e.g., spoiled gradient recalled (SPGR) acquisition) being commonly employed to achieve the electrode localization. It is recognized, however, that presently used post-implantation imaging techniques for locating the DBS electrode can lead to imperfect electrode localization, whether it be due to beam hardening artifacts in a CT image acquisition or due to susceptibility induced signal loss in a long-readout MR image acquisition. For example, physical electrode diameters of 1.27 mm appear as ~2.6 mm-wide signal blooms in CT images and ~3.8 mm-wide signal voids in MR images acquired with long-readouts. Thus, it can be seen that a location of the DBS electrode may differ between acquired CT images and MR images, with differences in location on the CT and MRI images exceeding 1 mm being routinely found. An accurate localization of the DBS electrode may thus be difficult to achieve via use of standardly employed post-operative CT and long-readout MR image acquisition techniques.

It would therefore be desirable to have a system and method capable of accurately detecting the location of a DBS electrode post-operatively, with such locating being achieved via a fast scan-time as compared to standard, long-readout MR image acquisition. It would also be desirable for such a system and method to provide for the locating of individual electrode contacts of the DBS electrode, so as to enable selective activation of specific contacts of the electrode during DBS treatment.

BRIEF DESCRIPTION OF THE INVENTION

In accordance with one aspect of the invention, a non-transitory computer readable storage medium is provided having stored thereon instructions that cause a processor to cause a magnetic resonance (MR) imaging system to acquire image data from a volume-of-interest in a subject or object that includes one or more electrodes implanted therein, the image data acquired via a zero echo time (ZTE) or ultrashort echo time (UTE) pulse sequence performed by the MR imaging system. The instructions further cause the processor to localize a respective electrode of the one or more electrodes within the volume-of-interest based on an analysis of the image data. In localizing the one or more electrodes, the processor is programmed to obtain at least one of a phase domain image and a magnitude domain image from the image data acquired via the ZTE or UTE pulse sequence, estimate an orientation of the electrode from the at least one of the phase domain image and the magnitude domain image, and identify at least one of an electrode center and locations of electrode contacts of the electrode, to localize the electrode within the volume-of-interest.

In accordance with another aspect of the invention, a method for localizing a deep brain stimulation (DBS) electrode in vivo in a patient is provided. The method includes obtaining MR image data from a volume-of-interest by way of a zero echo time (ZTE) or ultrashort echo time (UTE) pulse sequence performed by a magnetic resonance (MR) imaging system, with the MR image data comprising one or more of a phase domain image and a magnitude domain image acquired via analysis of signal dephasing during readout of the ZTE or UTE pulse sequence. The method also includes performing a multi-scale correlation-based analysis of the volume-of-interest to estimate at least one of an electrode center and electrode contact locations of the DBS electrode.

In accordance with yet another aspect of the invention, a system for localizing a deep brain stimulation (DBS) electrode in vivo in a subject or object is provided. The system includes a magnetic resonance (MR) imaging system having a plurality of gradient coils positioned about a bore of a magnet, an RF coil assembly configured to emit RF pulse sequences and arranged to receive resulting MR image data from a volume-of-interest in the subject or object, and a system control coupled to the plurality of gradient coils and the RF coil assembly, the system control programmed to control the RF coil assembly and the plurality of gradient coils to apply a zero echo time (ZTE) or ultrashort echo time (UTE) pulse sequence that generates the MR image data from signal dephasing during a readout of the ZTE or UTE pulse sequence. The system also includes a computer programmed to analyze at least one of a magnitude domain image or a phase domain image of the MR signals, perform a first up-sampling on the at least one of the magnitude domain image or phase domain image, estimate an orientation of the DBS electrode from the up-sampled at least one of the magnitude domain image or phase domain image, and identify at least one of an electrode center and electrode contact locations of the DBS electrode from the up-sampled at least one of the magnitude domain image or phase domain image.

Various other features and advantages will be made apparent from the following detailed description and the drawings.

BRIEF DESCRIPTION OF THE DRAWINGS

The drawings illustrate embodiments presently contemplated for carrying out the invention.

In the drawings:

FIG. 13 is a table listing mean position difference, standard deviation of position difference, minimum position difference, and maximum position difference of a SPGR to CT comparison and a ZTE (phase) to CT comparison.

DETAILED DESCRIPTION

In general, embodiments of the invention described herein are directed to a system and method for locating a DBS electrode post-operatively within a subject using a short readout MR imaging technique. Signal dephasing during readout in a ZTE or UTE sequence can be automatically analyzed either in the magnitude domain or in the phase domain to accurately locate the DBS electrode center and individual electrode contact locations with precision and efficiency.

Figure 1:
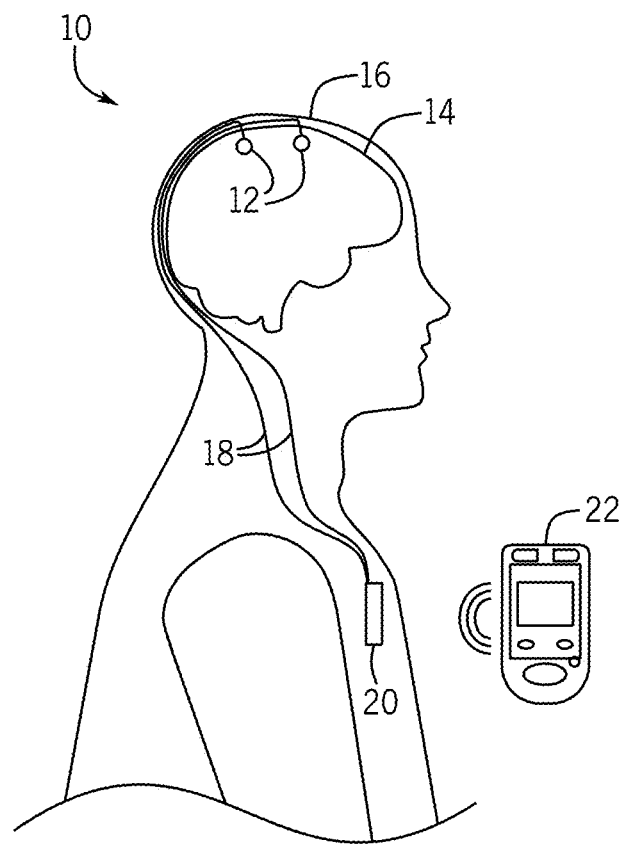
FIG. 1 is a schematic block diagram of a deep brain stimulation (DBS) detection system, according to an embodiment of the invention.

FIG. 1 depicts a DBS detection system 10 according to one embodiment of the invention. The DBS detection system 10 includes one or more leads or electrodes 12 surgically implanted within the one or more regions of the brain 14 of a subject or object that may be a patient 16, as shown in FIG. 1, or alternatively an animal or other inanimate object. For ease of reference, the subject or object is hereafter generally referred to as a patient. Each implanted electrode 12 is configured to apply stimulation signals to a targeted region of the brain 14. While two electrodes 12 are illustrated in FIG. 1, it will be understood that system 10 may include a single implanted electrode as well as three or more electrodes, each of which may be positioned and configured to facilitate unipolar or bipolar stimulation. According to certain embodiments, the electrodes may be of known construction, with Medtronic® 3387 and Medtronic® 3389 electrodes being common examples of electrodes often used for DBS treatments.

Each implanted electrode 12 is connected through an extension wire 18 that is passed under the skin of the patient 16 to a pulse generator 20 configured to deliver stimulation signals to electrodes 12. Pulse generator 20 may include a power supply (not shown) such as a battery or other type of power storage device and microelectronic circuitry (not shown) that may include hardware and/or software for generating and outputting stimulation signals in response to control signals or commands. In some embodiments, pulse generator 20 may further include a storage unit (not shown) that permits patient-specific data to be stored within the pulse generator 20.

In the illustrated embodiment, pulse generator 20 is an internal pulse generator that is implanted beneath the skin of the patient 16, such as, for example, under the clavicle as shown in FIG. 1. However, internal pulse generator 20 may be located elsewhere within the patient 16 in alternative embodiments such as, for example, lower in the chest or over the abdomen. As one non-limiting example, internal pulse generator 20 is an Activa PC Neurostimulator manufactured by Medtronic®. In alternative embodiments, pulse generator 20 may be an external device operationally coupled to implanted electrodes 12.

In the case of an implanted pulse generator, the pulse generator 20 is programmed with a wireless device 22 that is held over the skin of the patient 16 proximate the implanted location of the pulse generator 20. The programming of the pulse generator 20 defines the stimulation parameters of the DBS, which can be adjusted as the patient's condition changes over time. The circuitry within the pulse generator 20 generates pulse sequences in accordance with the stimulation parameters that send excitation signals to implanted electrodes 12. The stimulation can be provided in a periodic manner and at various currents, voltages, frequencies, and pulse widths based on the desired treatment.

Figure 2:
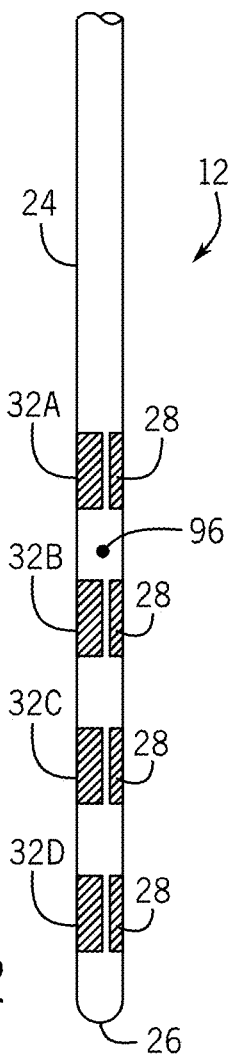
FIG. 2 is a side view of a DBS electrode used in the DBS detection system of FIG. 1, according to an embodiment of the invention.

A more detailed view of an implanted lead or electrode 12 of DBS detection system 10 is illustrated in FIG. 2, according to an exemplary embodiment. As shown in FIG. 2, electrode 12 includes a housing 24 extending along a length thereof and ending at a rounded distal tip 26. A plurality of contacts 28 are positioned along a length of electrode 12 and housing 24 at a plurality of defined contact levels 32. The housing 24 is constructed such that electrode 12 is formed as a substantially rigid component, so as to prevent the implanted electrode 12 from varying from the expected electrode shape. The electrode 12/housing 24 may be substantially cylindrical in shape. In other examples, electrode 12/housing 24 may be shaped differently than a cylinder. For example, the electrode 12/housing 24 may include one or more curves to reach target anatomical regions of the brain. In some examples, electrode 12/housing 24 may be similar to a flat paddle electrode or an electrode with a shape conformable for the patient. Also, in other examples, electrode 12/housing 24 may take any of a variety of different shapes.

As shown in FIG. 2, electrode 12 includes four contact levels 32 (includes levels 32A-32D) mounted at various lengths of housing 24, although it is recognized that electrode 12 may have more than four contact levels (e.g., eight contact levels). Contact levels 32A, 32B, 32C, and 32D are equally spaced along the axial length of housing 24 at different axial positions. Each contact level 32 may have two or more contacts 28 located at different angular positions around the circumference of housing 24. Contacts 28 of one circumferential location may be lined up on an axis parallel to the longitudinal axis of electrode 12. Alternatively, contacts 28 of different contact levels may be staggered around the circumference of housing 24. In addition, electrode 12 may include asymmetrical contact locations around the circumference of each electrode or contacts 28 of the same level that have different sizes. These contacts 28 may include semi-circular contacts 28 that may or may not be circumferentially aligned between contact levels 32.

In one embodiment, housing 24 may include a radiopaque stripe (not shown) along the outside of the housing 24. The radiopaque stripe corresponds to a certain circumferential location that allows electrode 12 to be imaged when implanted in the patient. Using the images of the patient, the clinician can use the radiopaque stripe as a marker for the exact orientation of electrode 12 within the brain of the patient. The orientation of electrode 12 may be needed to easily program the stimulation parameters by generating the correct contact configuration to match the stimulation field defined by the clinician. In other examples, a marking mechanism other than a radiopaque stripe may be used to identify the orientation of electrode 12. These marking mechanisms may include something similar to a tab, detent, or other structure on the outside of housing 24. In some examples, the clinician may note the position of markings along housing 24 during implantation to determine the orientation of the electrode within the patient.

Figure 3:
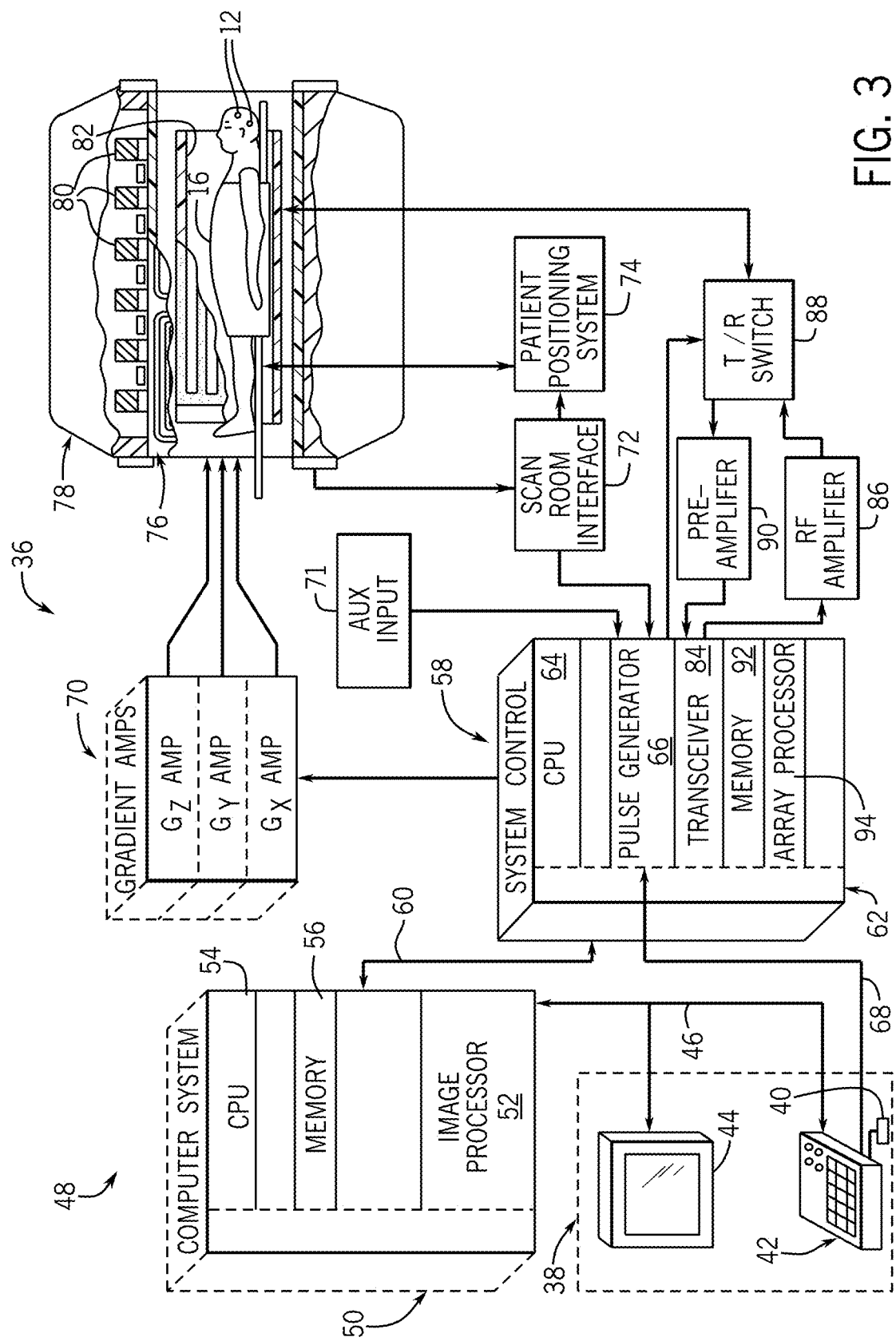
FIG. 3 is a schematic block diagram of an exemplary MR imaging system for use with an embodiment of the invention.

As previously described, it is necessary to be able to accurately locate the DBS electrode post-implantation for assessing surgery success in accurately implanting the electrode and for subsequently aiding device programming. According to an embodiment of the invention, such post-implantation locating is performed via the use of MR imaging system. An exemplary MR imaging system 36 useable with the DBS detection system 10 of FIG. 1 for localizing electrodes in the patient post-operatively is illustrated in FIG. 3, with the major components of the MR imaging system 36 being shown therein. The operation of the MR imaging system 36 is controlled for certain functions from an operator console 38, which in this example includes a keyboard or other input device 40, a control panel 42, and a display screen 44. The input device 40 can include a mouse, joystick, keyboard, track ball, touch activated screen, light wand, voice control, card reader, push-button, or any similar or equivalent input device, and may be used for interactive geometry prescription. The operator console 38 communicates through a link 46 with a separate computer system 48 that enables an operator to control the production and display of images on the display screen 44. The computer system 48 includes a number of modules which communicate with each other through a backplane 50. These modules include an image processor module 52, a CPU module 54 and a memory module 56, known in the art as a frame buffer for storing image data arrays. The computer system 48 communicates with a separate system control 58 through a high speed serial link 60.

The system control 58 includes a set of modules connected together by a backplane 62. These include a CPU module 64 and a pulse generator module 66 which connects to the operator console 38 through a serial link 68. It is through serial link 68 that the system control 58 receives commands from the operator to indicate the scan sequence that is to be performed. The pulse generator module 66 operates the system components to carry out the desired scan sequence and produces data which indicates the timing, strength and shape of the radio frequency (RF) pulses produced, and the timing and length of the data acquisition window. The pulse generator module 66 connects to a set of gradient amplifiers 70, to indicate the timing and shape of the gradient pulses that are produced during the scan. The pulse generator module 66 can also receive timing data through an auxiliary trigger input 71. And finally, the pulse generator module 66 connects to a scan room interface circuit 72 which receives signals from various sensors associated with the condition of the patient and the magnet system. It is also through the scan room interface circuit 72 that a patient positioning system 74 receives commands to move the patient to the desired position for the scan.

The gradient waveforms produced by the pulse generator module 66 are applied to the gradient amplifier system 70 having Gx, Gy, and Gz amplifiers. Each gradient amplifier excites a corresponding physical gradient coil in a gradient coil assembly generally designated 76 to produce the magnetic field gradients used for spatially encoding acquired signals. The gradient coil assembly 76 forms part of a resonance assembly 78 which includes a polarizing magnet 80 and a whole-body RF coil 82. A transceiver module 84 in the system control 58 produces pulses which are amplified by an RF amplifier 86 and coupled to the whole-body RF coil 82 by a transmit/receive switch 88. The resulting signals emitted by the excited nuclei in the patient may be sensed by the same whole-body RF coil 82 and coupled through the transmit/receive switch 88 to a preamplifier 90. The amplified MR signals are demodulated, filtered, and digitized in the receiver section of the transceiver module 84. The transmit/receive switch 88 is controlled by a signal from the pulse generator module 66 to electrically connect the RF amplifier 86 to the whole-body RF coil 82 during the transmit mode and to connect the preamplifier 90 to the whole-body RF coil 82 during the receive mode. The transmit/receive switch 88 can also enable a separate RF coil (for example, a surface coil) to be used in either the transmit or receive mode.

The MR signals picked up by the whole-body RF coil 82 are digitized by the transceiver module 84 and transferred to a memory module 92 in the system control 58. A scan is complete when an array of raw k-space data has been acquired in the memory module 92. This raw k-space data is rearranged into separate k-space data arrays for each image to be reconstructed, and each of these is input to an array processor 94 which operates to Fourier transform the data into an array of image data. This image data is conveyed through the serial link 60 to the computer system 48 where it is stored in memory. In response to commands received from the operator console 38 or as otherwise directed by the system software, this image data may be archived in long term storage or it may be further processed by the image processor module 52 and conveyed to the operator console 38 and presented on the display screen 44.

According to some embodiments of the invention, MR imaging system 36 is operated to enable optimized visualization and localization of the DBS electrodes 12 postoperatively within the patient 16, with acquisition of the image data and subsequent analysis and processing of the image data by computer system 48 being selectively controlled to achieve such optimization. With respect to image acquisition, the MR imaging system 36 is controlled to acquire images of a volume-of-interest (e.g., the head/brain region) that includes the electrodes 12 therein, with the images being acquired via a short readout MR image acquisition sequence that may be performed quickly and that minimizes signal dephasing during the acquisition. Therefore, according to exemplary embodiments, the MR imaging system 36 is operated to employ a zero echo time (ZTE) or ultrashort echo time (UTE) pulse sequence for image acquisition. In a ZTE or UTE pulse sequence, a very-short block pulse or half-sinc pulse, respectively, RF excitation signal is generated by pulse generator module 66 in order to allow subsequent data sampling at an ultrashort echo time being on the order of magnitude in micro seconds, e.g., 8 microseconds, with the gradients already being activated during the excitation in ZTE. Gradient echo acquisition may be employed to acquire gradient echoes and free induction decay (FID) signals and, in one embodiment, spin echo acquisition may be employed to acquire spin echo signals in instances where a refocusing (180°) is included in the pulse sequence, depending on the exact ZTE or UTE pulse sequence that is employed. With respect to analysis and processing of the acquired image data, an automated technique of segmentation and cross-correlations may be applied to the image data, such as by computer 48, to localize the electrode 12.

Figure 4:
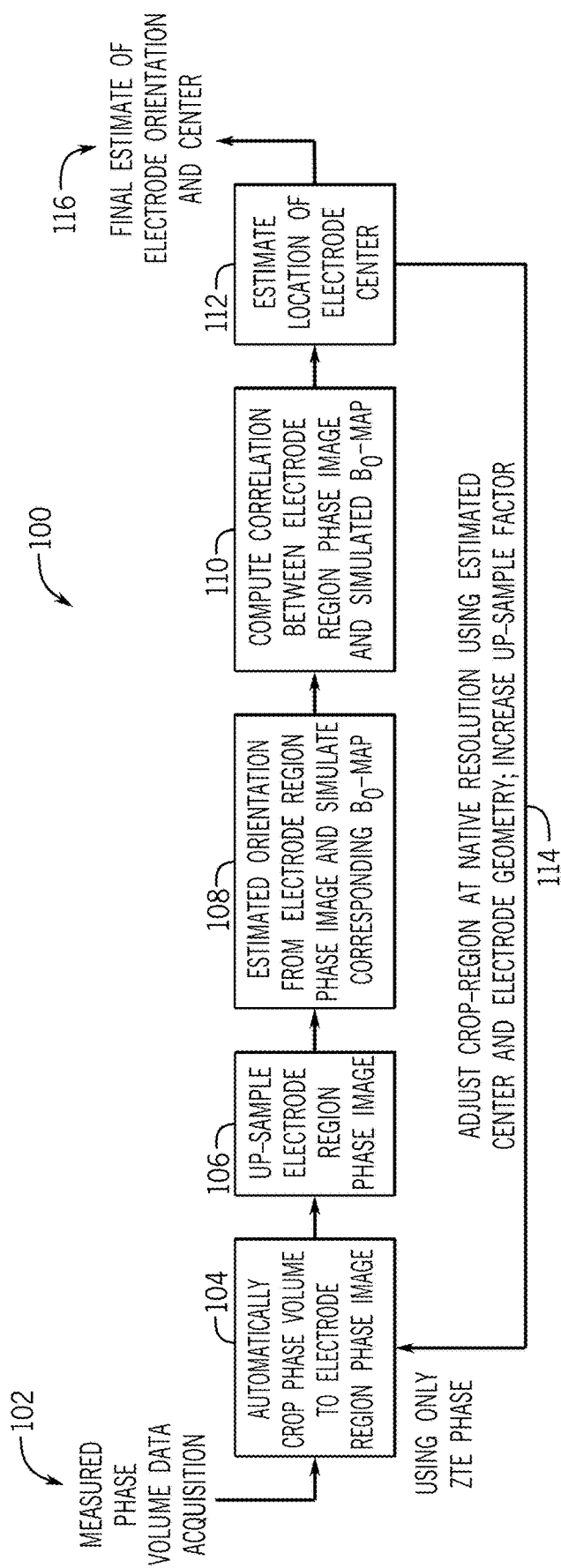
FIG. 4 is a flowchart illustrating a technique for localizing a DBS electrode post-operatively, according to an embodiment of the invention.
Figure 5:
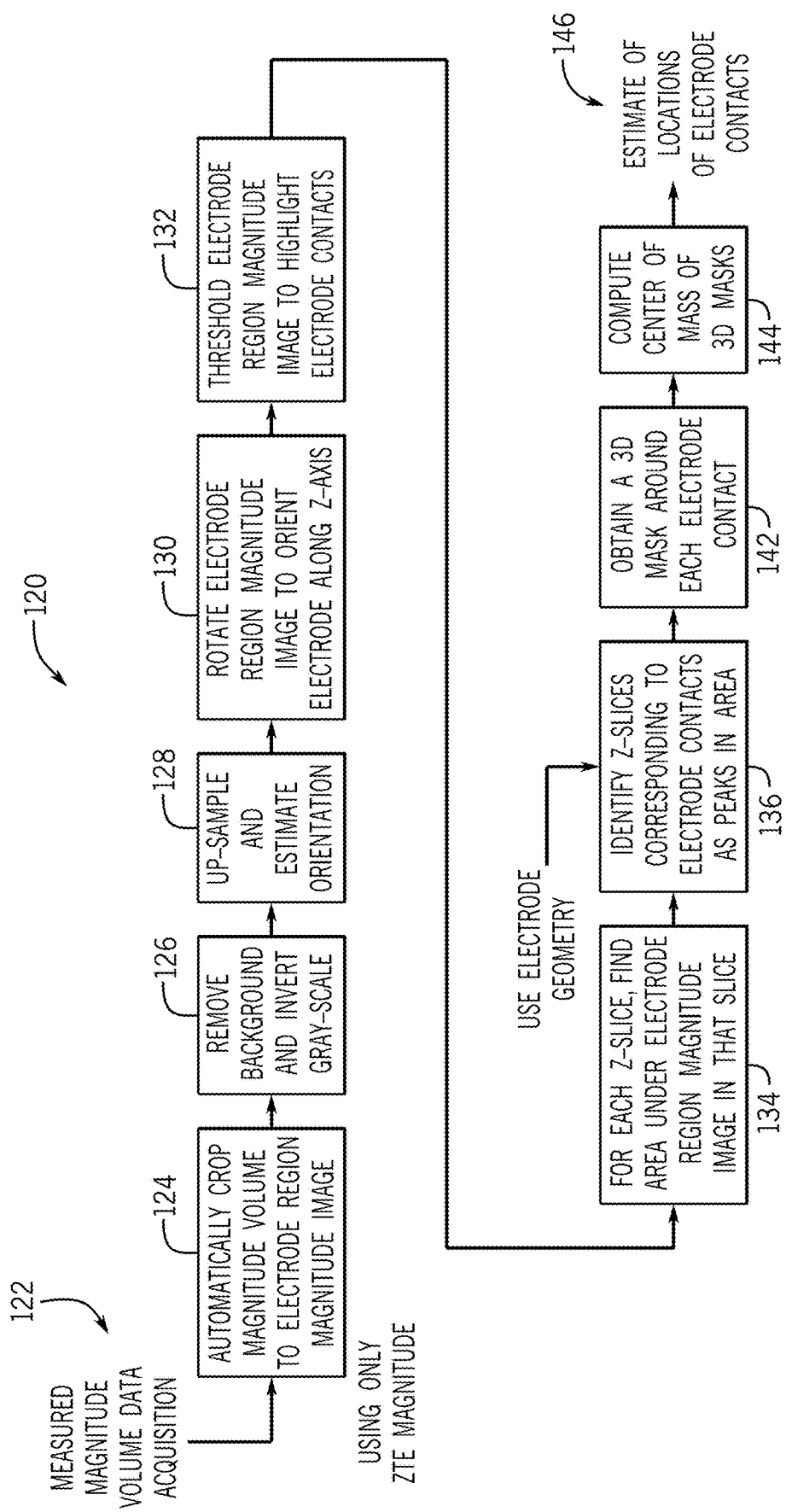
FIG. 5 is a flowchart illustrating a technique for localizing a DBS electrode post-operatively, according to another embodiment of the invention.
Figure 6:
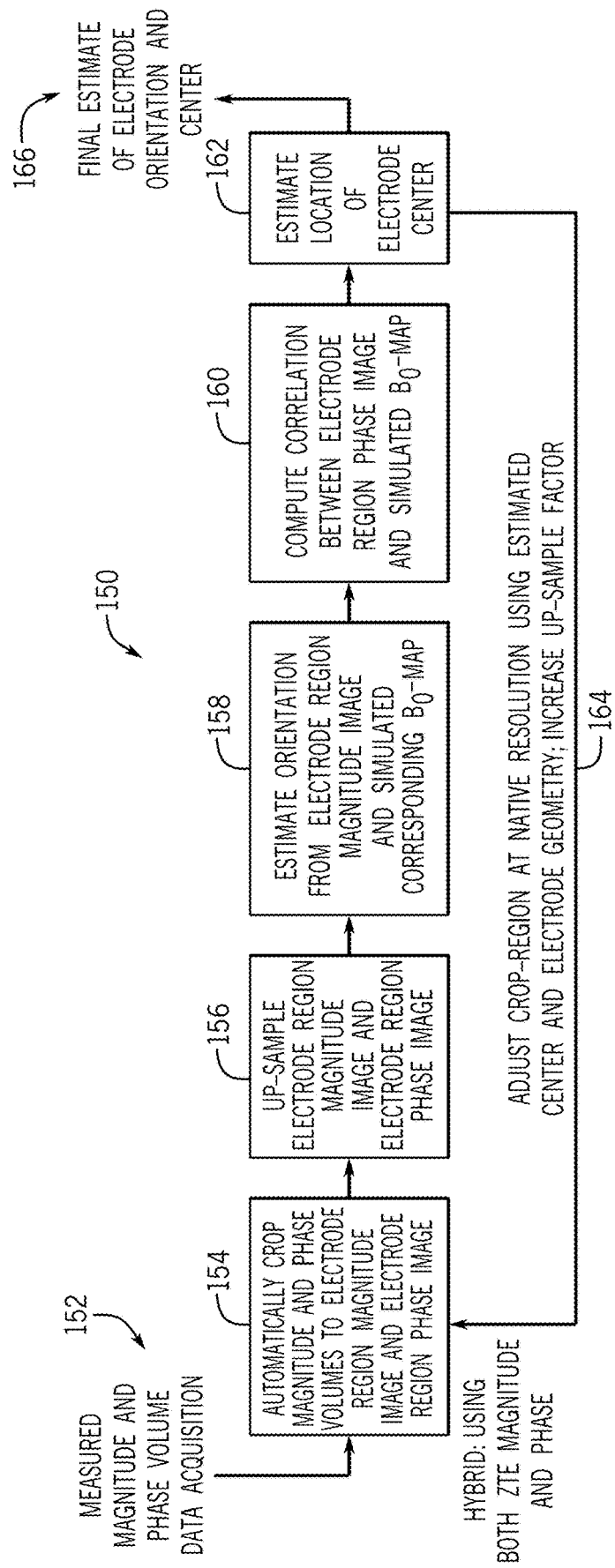
FIG. 6 is a flowchart illustrating a technique for localizing a DBS electrode post-operatively, according to another embodiment of the invention.
Figure 7:
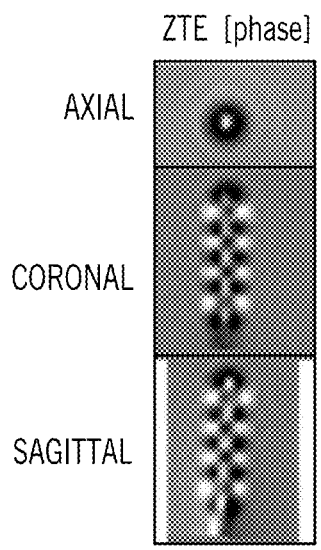
FIG. 7 illustrates phase domain images provided in axial, coronal, and sagittal slices, as generated for the technique of FIG. 4 and/or the technique of FIG. 6.

According to some embodiments of the invention, and in order to provide for visualization and localization of the DBS electrodes 12, signal dephasing during readout in the ZTE/UTE can be analyzed in the magnitude and/or or phase domain. More specifically, signal dephasing during readout in the ZTE/UTE can be analyzed in the magnitude and/or or phase domain in order to accurately and precisely locate a center of mass, or an electrode center, of a DBS electrode 12 (for example, electrode center 96, FIG. 2) and individual electrode contacts 28 of the DBS electrode 12. FIGS. 4-6 illustrate various DBS electrode localization techniques that may be performed that utilize signal dephasing in the phase domain, in the magnitude domain, or in both the phase and magnitude domains, according to embodiments of the invention. Additionally, FIGS. 7-11 illustrate various images and/or plots acquired and analyzed during the performing of the techniques of FIGS. 4-6, according to embodiments of the invention.

Referring first to FIG. 4, in conjunction with the elements of FIGS. 1-3 where appropriate, a technique 100 for localizing the DBS electrode 12 using only signal dephasing in the phase domain of a ZTE/UTE acquisition readout is shown according to one embodiment. The technique 100 begins at STEP 102 with acquisition of MR image data (via a ZTE/UTE scan sequence) for a measured phase volume providing a phase domain image of the volume-of-interest in the form of a plurality of axial (or sagittal or coronal or obliquely-oriented) slices of the volume, with it being recognized that signal dephasing during sequence readout, proportional to the electrode-induced field inhomogeneity, provides high-contrast visualization of the electrode 12 and of individual contacts 28 thereof. An example of phase domain images provided in axial, coronal, and sagittal slices are provided in FIG. 7. According to an exemplary embodiment, the phase volume is then automatically segmented (or "cropped") into smaller regions that each encompasses a DBS electrode 12 at STEP 104 such that each of a number of cropped phase volumes are provided—with these cropped phase volumes also being referred to as electrode regions or electrode region phase images. According to one embodiment, an image-thresholding and image-masking is used for performing the segmentation. It is recognized, however, that the segmenting/cropping of STEP 104 need not be performed in technique 100, according to other embodiments of the invention, and that the following steps in technique 100 set forth here below could be performed on the full phase volume rather than a cropped electrode region therein.

Figure 8:
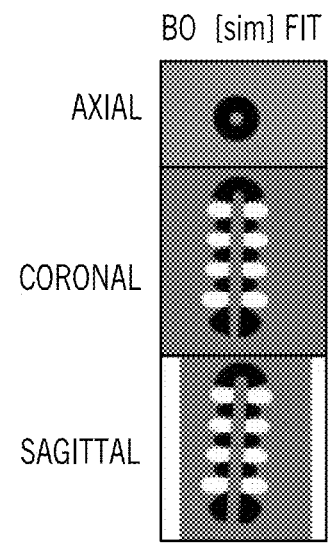
FIG. 8 illustrates simulated orientation dependent field inhomogeneity ($B_0$) maps provided in axial, coronal, and sagittal slices, as generated for the technique of FIG. 4 and/or the technique of FIG. 6.

In a next step of technique 100, an electrode region phase image (i.e., cropped phase volume) is then up-sampled with a 3D Fast Fourier Transform (FFT) being used for up-sampling at STEP 106, with the electrode region phase image being up-sampled by a scale factor of 0.5× to 10×, for example, such that the image resolution thereof is improved. An orientation of the electrode 12 is then estimated from the electrode region phase image and a corresponding orientation dependent field inhomogeneity ($B_0$) map is simulated, as indicated at STEP 108. Orientation of the electrode 12 may be estimated from the electrode region phase image using an image-thresholding, an image-masking, and a singular value decomposition (SVD), with it being recognized that in practice the electrode 12 will typically be oriented at an angle of 20° to 40°. For purposes of simulating a $B_0$ map, it is required that a model of the electrode 12 (e.g., model of a Medtronic 3387 electrode) be provided that accurately provides details on the geometry of the electrode 12, including outer dimensions, contact location/spacing, etc. The model of the electrode 12 also provides appropriate susceptibility values associated with the geometric model, with the model including a catalog of magnetic field disturbances ($B_0$) created by the electrode 12 as a function of its orientation. A $B_0$ map matching the scale/orientation of the electrode 12 can thus be simulated using the geometric model of the electrode 12 as an input, with FIG. 8 illustrating an exemplary $B_0$ map or image that may be generated at STEP 108. According to an embodiment, the volume inside the electrode 12 is set to zero, to reduce the impact of this noise-dominated region on localization.

Figure 9:
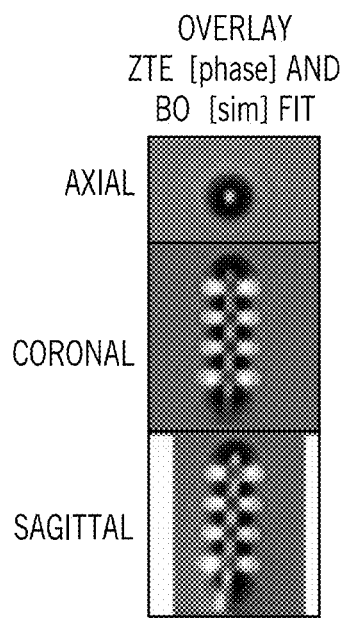
FIG. 9 illustrates overlays of the phase domain images and the simulated $B_0$-maps of FIGS. 7 and 8, as generated for the technique of FIG. 4 and/or the technique of FIG. 6.
Figure 10:
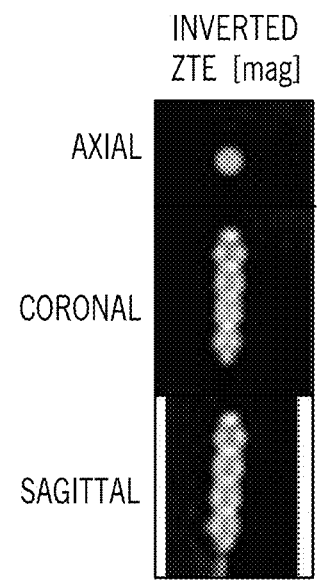
FIG. 10 illustrates magnitude domain images provided in axial, coronal, and sagittal slices, as generated for the technique of FIG. 5 and/or the technique of FIG. 6.

Upon completion of the electrode orientation estimation and the $B_0$ map simulation, the technique 100 proceeds to STEP 110, where a correlation between the phase domain image and the simulated $B_0$ map is computed. The cross-correlation may be performed via the use of a 3D FFT, for example, so as to provide for rapid computation of the cross-correlation. Cross-correlation between the phase domain image and simulated $B_0$ maps then provides for estimation of the electrode center 96 and extraction of the 3D location of electrode contacts 28 at STEP 112. The electrode center 96 is estimated by finding the translation maximizing the correlation between the simulated $B_0$-map and the phase domain image. An overlay of the phase domain image and the simulated $B_0$-map is illustrated in FIG. 9.

As shown in FIG. 4, upon estimation of the electrode center 96 and extraction of the 3D location of electrode contacts 28 at STEP 112, the technique 100 continues by looping back to STEP 104, as indicated at 114, such that technique 100 is performed as a multi-scale, correlation-based approach for localization. In looping back to STEP 104, the cropped phase volume (electrode region phase image) is adjusted at a native resolution using the estimated electrode center 96 and the known/modeled electrode geometry, with the electrode center value being used as a starting point for the next scale. The up-sample factor is adjusted at STEP 106 and another iteration of STEPS 108-112 is performed using the adjusted electrode region phase image and up-sampling values to identify a revised electrode center 96 and location of contacts 28. A desired number of iterations may be performed until a final estimate of the electrode orientation and center 96 is provided at STEP 116. In one embodiment, the final estimate of the electrode orientation and center may be determined after the performing of a pre-determined number of iterations of technique 100. In another embodiment, the final estimate of the electrode orientation and center may be determined when the estimated electrode orientation and center in successive iterations differ by an amount less than a pre-determined threshold. An accurate and precise localization of the electrode 12 may thus be achieved in this manner.

Referring now to FIG. 5, in conjunction with the elements of FIGS. 1-3 where appropriate, a technique 120 for localizing the DBS electrode 12 using only signal dephasing in the magnitude domain of a ZTE/UTE acquisition readout is shown according to one embodiment. The technique 120 begins at STEP 122 with acquisition of MR image data (via a ZTE/UTE scan sequence) for a measured magnitude volume providing a magnitude domain image of the volume-of-interest in the form of a plurality of axial (or sagittal or coronal or obliquely-oriented) slices of the volume.

In continuing technique 120, the magnitude domain image is next automatically segmented or "cropped" into smaller regions that each encompasses a DBS electrode 12 at STEP 124, such that each of a number of cropped magnitude volumes are provided—with these cropped magnitude volumes also being referred to as electrode regions or electrode region magnitude images. Upon segmenting/cropping, the background of the electrode region magnitude image is removed and the gray-scale of the image is inverted at STEP 126, so as to generate pseudo-positive contrast images having improved image clarity. An example of inverted gray-scaled magnitude domain images provided in axial, coronal, and sagittal slices are provided in FIG. 10. According to one embodiment, the pseudo-positive contrast image is obtained by first generating an object mask using region growing and dilation, inverting the masked images, fitting the remaining background signal with a point-wise polynomial interpolation function, and subtracting this smoothed background from the images. Upon generation of the cropped gray-scale electrode region magnitude image, the image is then up-sampled at STEP 128, with the image being up-sampled by a scale factor of 2× to 10×, for example, such that the image resolution of the image is improved. Also at STEP 128, an orientation of the electrode 12 is estimated from the electrode region magnitude image, such as via an image-thresholding, an image-masking, and a singular value decomposition (SVD) of a morphological mask obtained by thresholding the electrode region magnitude image, with it being recognized that in practice the electrode 12 will typically be oriented at an angle of 20° to 40°.

Figure 11:
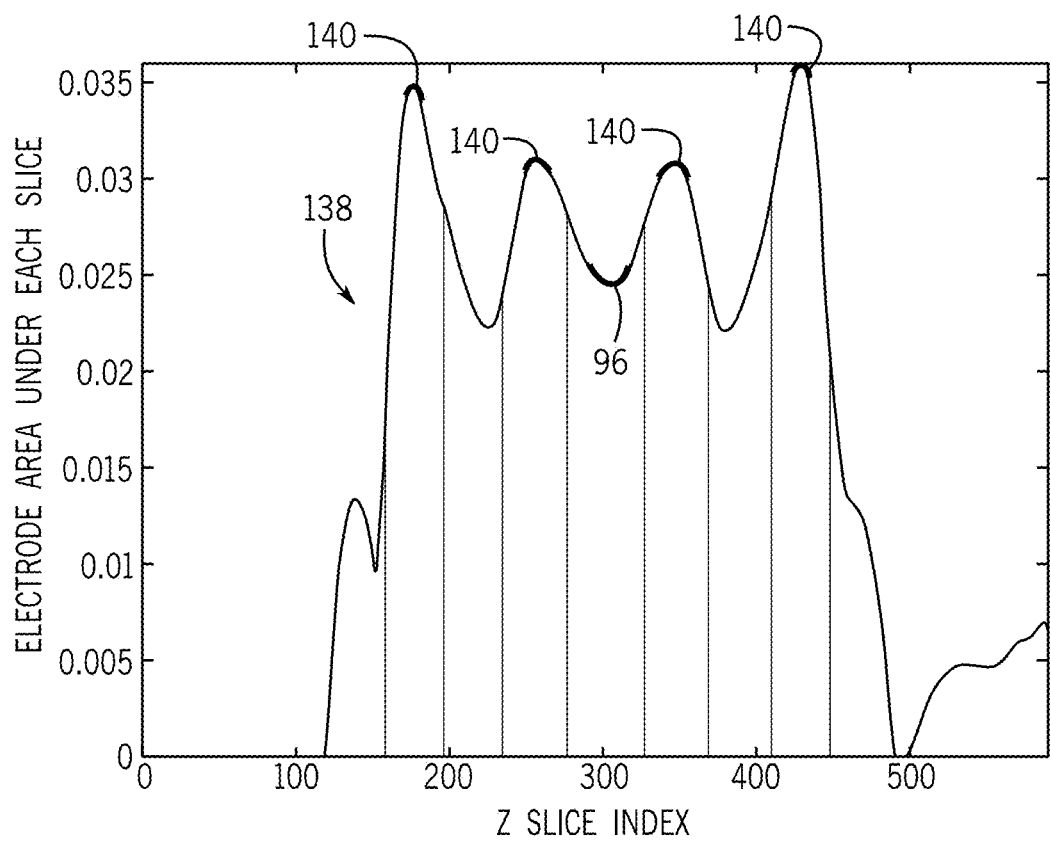
FIG. 11 is a graph illustrating the electrode area under a z-slice (signal void) in the magnitude domain as a function of the z-slice index.
Figure 12A:
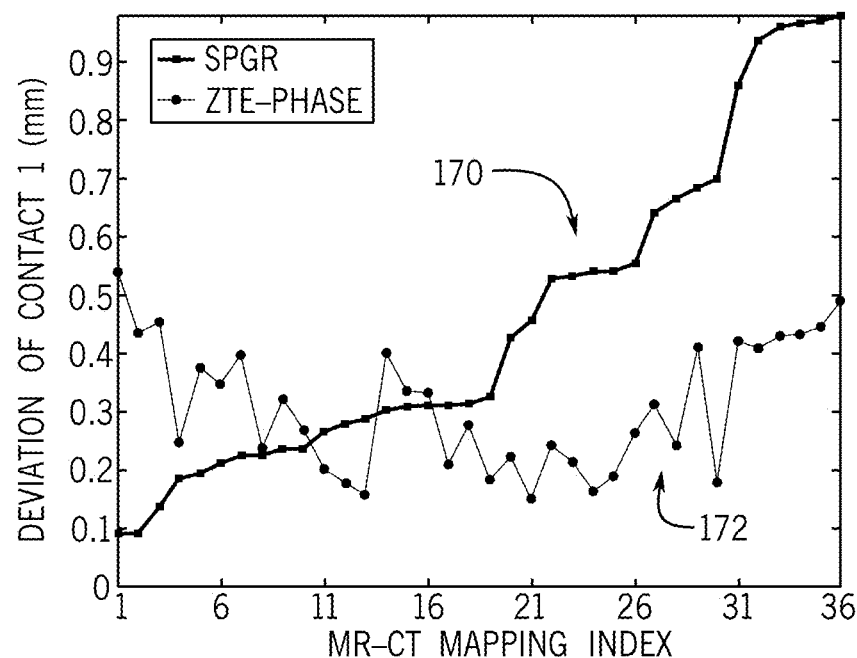
FIGS. 12A-12D are graphs illustrating differences (in Euclidean norm) between electrode contact locations in CT imaging and the projected contact location from SPGR and ZTE image acquisitions.
Figure 12B:
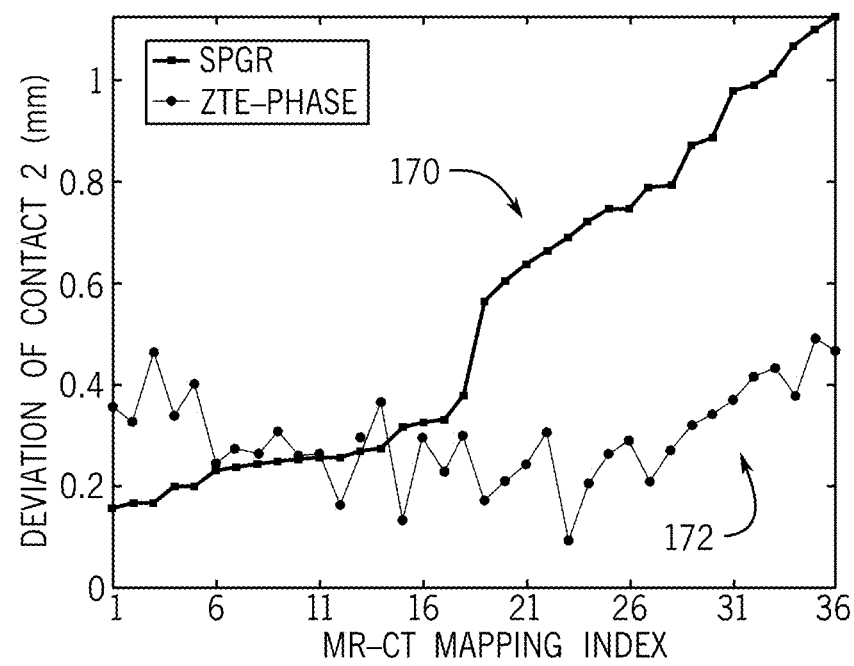
Figure 12C:
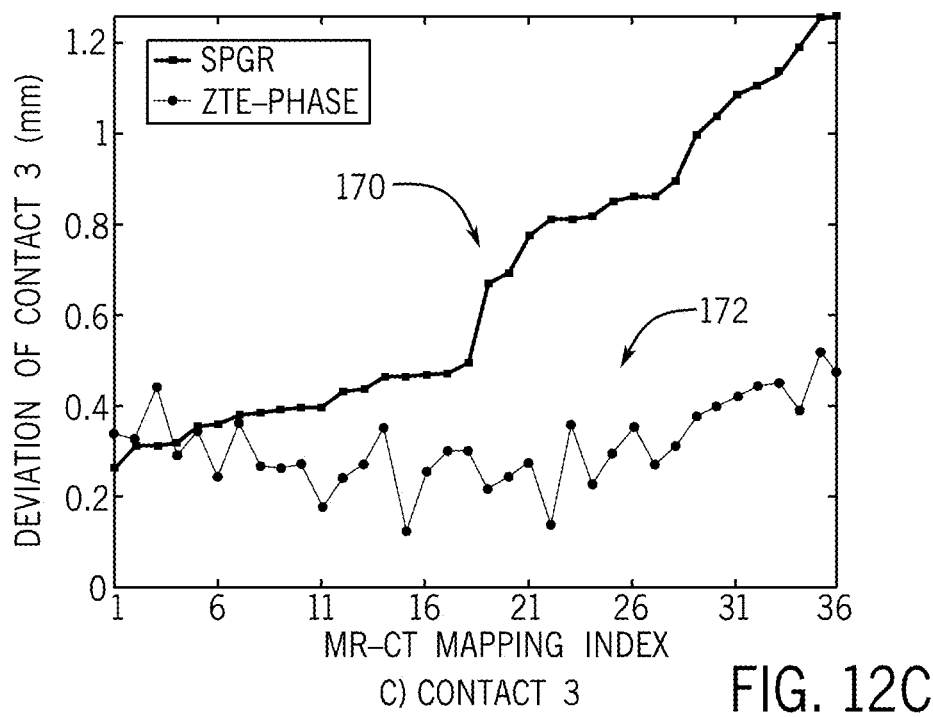
Figure 12D:
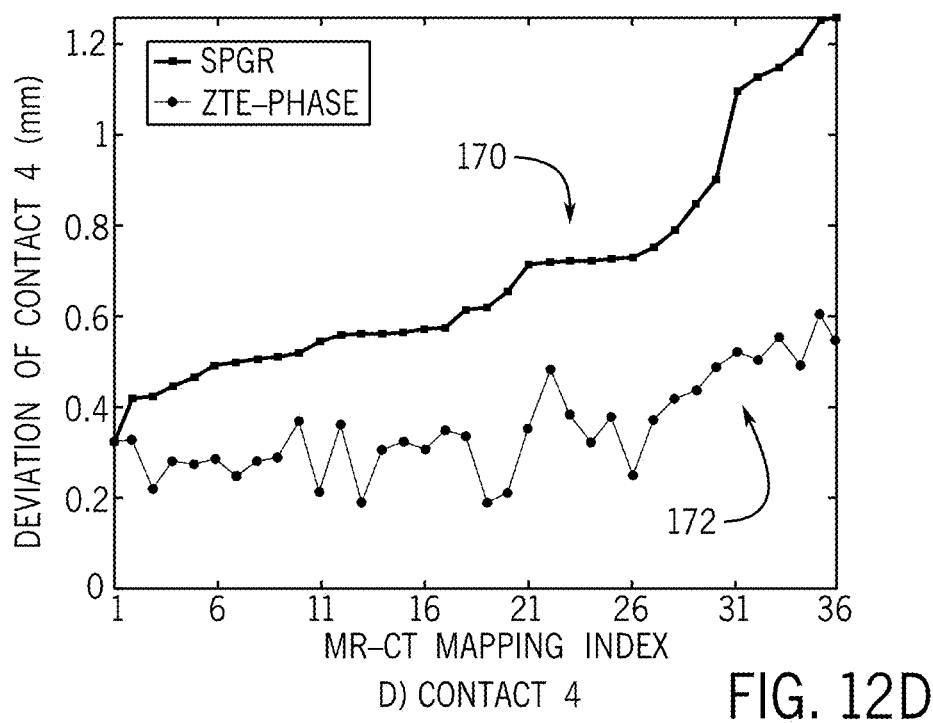

Upon estimation of the electrode orientation, the technique 120 continues at STEP 130 with the electrode region magnitude image being rotated such that the electrode 12 is oriented along the z-axis (i.e., along 0°). The electrode region magnitude image is then thresholded at STEP 132 (i.e., threshold the magnitude volume) in order to highlight the contacts 28 of the electrode 12. For each z-slice of the electrode profile, the area under the thresholded electrode region magnitude image for that slice is then found at STEP 134, with z-slices corresponding to electrode contacts 28 being identified at STEP 136 based on analysis of the z-slices and a knowledge of the electrode geometry. An illustration of the area under the signal void (inverted grayscale) in the electrode region magnitude image as a function of slice index is shown in FIG. 11. In the plot/image, it can be seen that for an electrode area under each slice—identified by plot 138—peaks 140 are present in the image that identify z-slices that correspond to electrode center 96/contacts 28. These peaks 140 can be automatically extracted in order to identify the z-slices corresponding to electrode contacts 28 at STEP 136.

In a next step of technique 120, and upon identification of z-slices of the electrode profile corresponding to electrode contacts 28, a 3D mask is obtained around each electrode contact at STEP 142, such as via a region growing and dilation technique. Using these 3D masks of the electrode contacts 28, the center of mass of each of the 3D masks is then computed at STEP 144. The center of mass calculations are then used to estimate the 3D locations of the contacts 28 at STEP 146—with these locations then also enabling determining of the electrode center 96.

Referring now to FIG. 6, in conjunction with the elements of FIGS. 1-3 where appropriate, a technique 150 for localizing the DBS electrode 12 using signal dephasing in both the phase domain and the magnitude domain of a ZTE/UTE acquisition readout is shown according to one embodiment. The technique 150 begins at STEP 152 with acquisition of MR image data (via a ZTE/UTE scan sequence) for a measured phase and magnitude volume (i.e., phase domain images and magnitude domain images) providing a phase domain image and a magnitude domain image of the volume-of-interest, with examples of phase and magnitude domain images provided in axial, coronal, and sagittal slices provided in FIGS. 7 and 10. According to an exemplary embodiment, the phase domain image and magnitude domain image are then automatically segmented (or "cropped") into smaller regions that each encompasses a DBS electrode 12 at STEP 154 such that each of a number of cropped phase volumes and magnitude volumes are provided—with these cropped phase volumes and magnitude volumes also being referred to as electrode region phase images and electrode region magnitude images. An image-thresholding and image-masking is used for performing the segmentation, according to one embodiment. It is recognized, however, that the segmenting/cropping of STEP 104 need not be performed in technique 150, according to other embodiments of the invention, and that the following steps in technique 150 set forth here below could be performed on the full phase volume rather than a cropped electrode region therein.

In a next step of technique 150, the electrode region phase images and electrode region magnitude images are up-sampled with a 3D FFT at STEP 156, with the images being up-sampled by a scale factor of 0.5× to 10×, for example, such that the image resolution of the images is improved. An orientation of the electrode 12 is then estimated within an up-sampled electrode region phase image and a corresponding orientation dependent field inhomogeneity ($B_0$) map is simulated, as indicated at STEP 158. Orientation of the electrode 12 may be estimated from the electrode region phase image using an image-thresholding, an image-masking, and a singular value decomposition (SVD), with it being recognized that in practice the electrode 12 will typically be oriented at an angle of 20° to 40°. For purposes of simulating a $B_0$ map, it is required that a geometric model of the electrode 12 (e.g., model of a Medtronic® 3387 electrode) be provided that accurately provides details on the geometry of the electrode 12, including outer dimensions, contact location/spacing, etc., as well as provides appropriate susceptibility values associated with the geometric model. A $B_0$ map matching the scale/orientation of the electrode 12 can thus be simulated using the geometric model of the electrode 12 as an input, with FIG. 8 illustrating an exemplary $B_0$ map or image that may be generated at STEP 158.

Upon completion of the electrode orientation estimation and the $B_0$ map simulation, the technique 150 proceeds to STEP 160, where a correlation between the electrode region phase image and the simulated $B_0$ map is computed. The cross-correlation may be performed via the use of a 3D FFT, for example, so as to provide for rapid computation of the cross-correlation. Cross-correlation between the ZTE-phase and simulated $B_0$ maps then provides for estimation of the electrode center 96 and extraction of the 3D location of electrode contacts 28 at STEP 162. The electrode center 96 is estimated by finding the translation maximizing the correlation between the simulated $B_0$-map and the ZTE/UTE phase domain image. An overlay of the ZTE/UTE phase domain image and the simulated $B_0$-map is illustrated in FIG. 9.

As shown in FIG. 6, upon estimation of the electrode center 96 and extraction of the 3D location of electrode contacts 28 at STEP 162, the technique 150 continues by looping back to STEP 154, as indicated at 164, such that technique 150 is performed as a multi-scale, correlation-based approach for localization. In looping back to STEP 154, the cropped ZTE phase volume is adjusted at a native resolution using the estimated electrode center 96 and the known/modeled electrode geometry, with the electrode center value being used as a starting point for the next scale. The up-sample factor is increased at STEP 156 and another iteration of STEPS 158-162 is performed with the updated cropping and up-sampling values to identify a revised electrode center 96 and location of contacts 28. A number of iterations may be performed until a final estimate of the electrode orientation and center 96 is provided at STEP 166. In one embodiment, the final estimate of the electrode orientation and center may be determined after the performing of a pre-determined number of iterations of technique 150. In another embodiment, the final estimate of the electrode orientation and center may be determined when the estimated electrode orientation and center in successive iterations differ by an amount less than a pre-determined threshold. An accurate and precise localization of the electrode 12 may thus be achieved in this manner.

Accordingly, embodiments of the present invention beneficially provide an apparatus and method for MRI-based electrode visualization and localization of a DBS electrode post-surgery. The apparatus and method provide for the locating of the electrode center and the locating of individual electrode contacts of the DBS electrode, with the locating of individual electrode contacts enabling selective activation of specific contacts of the electrode during DBS treatment. The visualization and localization of the DBS electrode is achieved via a ZTE or UTE imaging technique, so as to provide a fast scan-time as compared to standard, long-readout MR image acquisition (e.g., SPGR) and as an alternative to CT imaging. The ZTE/UTE imaging technique provides higher localization accuracy and precision and smaller standard deviations as compared to SPGR—when compared to CT imaging localization. FIGS. 12A-12D illustrate the improvement in accuracy and precision of the ZTE/UTE imaging technique as compared to an SPGR imaging technique—with the graph showing differences (in Euclidean norm) between each electrode contact location in CT and the projected electrode contact location from SPGR and ZTE acquisitions onto CT. Thirty-six data points (corresponding to 6 MR×6 CT=36 registrations) were arbitrarily arranged from smallest to largest for SPGR-CT differences 170, and the corresponding ZTE-CT differences 172 are displayed for the exact same locations/registrations. FIG. 13 is a table setting forth a summary of localization accuracy/precision for SPGR and ZTE compared to CT—with mean position difference, standard deviation of position difference, minimum position difference, and maximum position difference being included therein. As can be seen in FIG. 13, electrode localization errors for the electrode center localization do not exceed 0.52 mm in the ZTE/UTE imaging technique as compared to electrode localization errors of 1.49 mm in SPGR. Thus, it can be seen that the techniques of the present invention that employ ZTE/UTE based localization provide an improvement compared to a conventional SPGR based localization approach and solve challenges faced in the art regarding scan-time issues and localization accuracy issues.

A technical contribution for the disclosed method and apparatus is that it provides for a computer implemented system and method for post-implantation localization of a DBS electrode. An MRI-based electrode visualization and localization method is employed that utilizes ZTE or UTE to acquire images of the electrode. Signal dephasing during readout in the ZTE/UTE sequence is automatically analyzed in the magnitude domain and/or in the phase domain to accurately and precisely locate the DBS electrode center and individual contacts of the electrode.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, according to one embodiment of the invention, a non-transitory computer readable storage medium is provided having stored thereon instructions that cause a processor to cause a magnetic resonance (MR) imaging system to acquire image data from a volume-of-interest in a subject or object that includes one or more electrodes implanted therein, the image data acquired via a zero echo time (ZTE) or ultrashort echo time (UTE) pulse sequence performed by the MR imaging system. The instructions further cause the processor to localize a respective electrode of the one or more electrodes within the volume-of-interest based on an analysis of the image data. In localizing the one or more electrodes, the processor is programmed to obtain at least one of a phase domain image and a magnitude domain image from the image data acquired via the ZTE or UTE pulse sequence, estimate an orientation of the electrode from the at least one of the phase domain image and the magnitude domain image, and identify at least one of an electrode center and locations of electrode contacts of the electrode, to localize the electrode within the volume-of-interest.

According to another embodiment of the invention, a method for localizing a deep brain stimulation (DBS) electrode in vivo in a patient is provided. The method includes obtaining MR image data from a volume-of-interest by way of a zero echo time (ZTE) or ultrashort echo time (UTE) pulse sequence performed by a magnetic resonance (MR) imaging system, with the MR image data comprising one or more of a phase domain image and a magnitude domain image acquired via analysis of signal dephasing during readout of the ZTE or UTE pulse sequence. The method also includes performing a multi-scale correlation-based analysis of the volume-of-interest to estimate at least one of an electrode center and electrode contact locations of the DBS electrode.

According to yet another embodiment of the invention, a system for localizing a deep brain stimulation (DBS) electrode in vivo in a subject or object is provided. The system includes a magnetic resonance (MR) imaging system having a plurality of gradient coils positioned about a bore of a magnet, an RF coil assembly configured to emit RF pulse sequences and arranged to receive resulting MR image data from a volume-of-interest in the subject or object, and a system control coupled to the plurality of gradient coils and the RF coil assembly, the system control programmed to control the RF coil assembly and the plurality of gradient coils to apply a zero echo time (ZTE) or ultrashort echo time (UTE) pulse sequence that generates the MR image data from signal dephasing during a readout of the ZTE or UTE pulse sequence. The system also includes a computer programmed to analyze at least one of a magnitude domain image or a phase domain image of the MR signals, perform a first up-sampling on the at least one of the magnitude domain image or phase domain image, estimate an orientation of the DBS electrode from the up-sampled at least one of the magnitude domain image or phase domain image, and identify at least one of an electrode center and electrode contact locations of the DBS electrode from the up-sampled at least one of the magnitude domain image or phase domain image.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A non-transitory computer readable storage medium having stored thereon instructions that cause a processor to:
    cause a magnetic resonance (MR) imaging system to acquire image data from a volume-of-interest in a subject or object that includes one or more electrodes implanted therein, the image data acquired via a zero echo time (ZTE) or ultrashort echo time (UTE) pulse sequence performed by the MR imaging system; and
    localize a respective electrode of the one or more electrodes within the volume-of-interest based on an analysis of the image data, wherein in localizing the respective electrode, the processor is programmed to:
        obtain at least one of a phase domain image and a magnitude domain image from the image data acquired via the ZTE or UTE pulse sequence;
        estimate an orientation of the electrode from the at least one of the phase domain image and the magnitude domain image; and
        identify at least one of an electrode center and locations of electrode contacts of the electrode, to localize the electrode within the volume-of-interest.

2. The non-transitory computer readable storage medium of claim 1 wherein, in obtaining at least one of a phase domain image and a magnitude domain image from the image data, the processor is programmed to obtain just the phase domain image from the image data, for localizing the electrode.

3. The non-transitory computer readable storage medium of claim 2 wherein, in localizing the one or more electrodes, the processor is programmed to:
    perform a first up-sampling on the phase domain image;
    estimate the orientation of the electrode within the phase domain image;
    generate a simulated orientation-dependent field inhomogeneity ($B_0$) map from a software model of the electrode and based on the estimated orientation of the electrode;
    compute a correlation between the $B_0$ map and the phase domain image to estimate the at least one of the electrode center and the locations of the electrode contacts of the electrode.

4. The non-transitory computer readable storage medium of claim 3 wherein the processor is programmed to estimate the at least one of the electrode center and the locations of the electrode contacts of the electrode by finding a translation value maximizing the correlation between the $B_0$ map and the phase domain image.

5. The non-transitory computer readable storage medium of claim 3 wherein the processor is programmed to find the translation value maximizing the correlation between the $B_0$ map and the phase domain image via a 3D Fast Fourier Transform (FFT).

6. The non-transitory computer readable storage medium of claim 3 wherein the software model of the electrode is stored on the processor and wherein the software model includes a geometric model of the electrode and a catalog of susceptibility values associated with the geometric model comprising magnetic field disturbances created by the electrode as a function of the orientation of the electrode.

7. The non-transitory computer readable storage medium of claim 3 wherein the processor is programmed to crop the phase domain image to provide an electrode region phase image, with the first up-sampling and the estimation of the electrode orientation being performed on the electrode region phase image and with the correlation being computed between the $B_0$ map and the electrode region phase image.

8. The non-transitory computer readable storage medium of claim 7 wherein the processor is further programmed to:
adjust a cropping of the electrode region phase image based on the estimated at least one of the electrode center and locations of the electrode contacts of the electrode to provide an adjusted electrode region phase image;
perform a second up-sampling on the adjusted electrode region phase image at a higher up-sampling value than the first up-sampling;
re-estimate the orientation of the electrode within the adjusted electrode region phase image;
generate an adjusted simulated orientation-dependent field inhomogeneity ($B_0$) map from the software model of the electrode and based on the re-estimated orientation of the electrode; and
compute an adjusted correlation between the adjusted $B_0$ map and the adjusted electrode region phase image to re-estimate the at least one of the electrode center and the locations of the electrode contacts of the electrode.

9. The non-transitory computer readable storage medium of claim 1 wherein, in localizing the one or more electrodes, the processor is programmed to compute both the magnitude domain image and the phase domain image from the image data for localizing the electrode.

10. The non-transitory computer readable storage medium of claim 9 wherein the processor is programmed to:
perform a first up-sampling on the phase domain image and magnitude domain image;
estimate the orientation of the electrode from the magnitude domain image;
generate a simulated orientation-dependent field inhomogeneity ($B_0$) map from a software model of the electrode and based on the estimated orientation of the electrode; and
compute a correlation between the $B_0$ map and the phase domain image to estimate the at least one of the electrode center and the locations of the electrode contacts of the electrode.

11. The non-transitory computer readable storage medium of claim 10 wherein the processor is programmed to crop both the magnitude domain image and the phase domain image to provide an electrode region phase image and an electrode region magnitude image, with the first up-sampling being performed on the electrode region phase image and the estimation of the electrode orientation being performed on the electrode region magnitude image, and with the correlation being computed between the $B_0$ map and the electrode region phase image.

12. The non-transitory computer readable storage medium of claim 1 wherein, in localizing the one or more electrodes, the processor is programmed to compute the magnitude domain image from the image data for localizing the electrode.

13. The non-transitory computer readable storage medium of claim 12 wherein, in localizing the one or more electrodes, the processor is programmed to:
remove background noise and invert a gray-scale of the magnitude domain image;
up-sample the magnitude domain image;
estimate the orientation of the electrode in the magnitude domain image;
rotate the magnitude domain image to orient the electrode along a z-axis;
perform a thresholding of the magnitude domain image to highlight electrode contacts of the electrode; and
identify the at least one of the electrode center and the locations of the electrode contacts of the electrode based on the thresholded magnitude domain image.

14. The non-transitory computer readable storage medium of claim 13 wherein, in identifying the at least one of the electrode center and the locations of the electrode contacts of the electrode based on the thresholded magnitude domain image, the processor is programmed to:
determine an area under a signal-void in the thresholded magnitude domain image for each of a number of z-slices of the electrode;
identify z-slices corresponding to the electrode contacts based on analysis of the number of z-slices and a known geometry of the electrode;
obtain a 3D mask around each of the electrode contacts;
determine a center of mass for the 3D mask around each of the electrode contacts; and
identify the at least one of the electrode center and the locations of the electrode contacts of the electrode based on the determined center of mass of the 3D mask around each of the electrode contacts.

15. The non-transitory computer readable storage medium of claim 13 wherein processor is programmed to estimate the orientation of the electrode via a singular value decomposition (SVD) of the magnitude domain image.

16. The non-transitory computer readable storage medium of claim 13 wherein the processor is programmed to crop the magnitude domain image to provide an electrode region magnitude image, with the removal of background noise, the gray-scale inversion, the up-sampling, the estimation of the electrode orientation, the rotating of the electrode, and the thresholding being performed on the electrode region magnitude image.

17. A method for localizing a deep brain stimulation (DBS) electrode in vivo in a subject or object, the method comprising:
obtaining MR image data from a volume-of-interest by way of a zero echo time (ZTE) or ultrashort echo time (UTE) pulse sequence performed by a magnetic resonance (MR) imaging system, with the MR image data comprising one or more of a phase domain image and a magnitude domain image acquired via analysis of signal dephasing during readout of the ZTE or UTE pulse sequence; and
performing a multi-scale correlation-based analysis of the volume-of-interest to estimate at least one of an electrode center and electrode contact locations of the DBS electrode.

18. The method of claim 17 wherein performing the multi-scale correlation-based analysis comprises:
cropping the volume-of-interest to define an electrode region, the electrode region comprising an electrode region phase image and an electrode region magnitude image;
performing a first up-sampling on the electrode region phase image;
estimating an orientation of the electrode within the electrode region;
generating a simulated orientation-dependent field inhomogeneity ($B_0$) map from a software model of the electrode and based on the estimated orientation of the electrode;

compute a correlation between the $B_0$ map and the electrode region phase image to estimate the at least one of the electrode center and the electrode contact locations of the electrode.

19. The method of claim 18 wherein estimating the orientation of the electrode within the electrode region comprises performing a singular value decomposition (SVD) of the electrode region magnitude image.

20. The method of claim 18 wherein estimating the at least one of the electrode center and the electrode contact locations of the electrode comprises finding a translation value maximizing the correlation between the $B_0$ map and the electrode region phase image.

21. The method of claim 18 wherein performing the multi-scale correlation-based analysis comprises:
   re-cropping the electrode region based on the estimated at least one of the electrode center and electrode contact locations of the electrode to provide an adjusted electrode region, the adjusted electrode region comprising an adjusted electrode region phase image and an adjusted electrode region magnitude image;
   performing a second up-sampling on the adjusted electrode region phase image at a higher value than the first up-sampling;
   re-estimating the orientation of the electrode within the adjusted electrode region magnitude image;
   generating a simulated orientation-dependent field inhomogeneity ($B_0$) map from the software model of the electrode and based on the re-estimated orientation of the electrode; and
   computing a correlation between the $B_0$ map and the adjusted electrode region phase image to re-estimate the at least one of the electrode center and the electrode contact locations of the electrode.

22. A system for localizing a deep brain stimulation (DBS) electrode in vivo in a subject or object, the system comprising:
   a magnetic resonance (MR) imaging system including:
      a plurality of gradient coils positioned about a bore of a magnet;
      an RF coil assembly configured to emit RF pulse sequences and arranged to receive resulting MR image data from a volume-of-interest in the subject or object; and
      a system control operationally coupled to the plurality of gradient coils and the RF coil assembly, the system control programmed to control the RF coil assembly and the plurality of gradient coils to apply a zero echo time (ZTE) or ultrashort echo time (UTE) pulse sequence that generates the MR image data from signal dephasing during a readout of the ZTE or UTE pulse sequence; and
   a computer programmed to:
      analyze at least one of a magnitude domain image or a phase domain image of the MR image data;
      perform a first up-sampling on the at least one of the magnitude domain image or phase domain image;
      estimate an orientation of the DBS electrode from the up-sampled at least one of the magnitude domain image or phase domain image; and
      identify at least one of an electrode center and electrode contact locations of the DBS electrode from the up-sampled at least one of the magnitude domain image or phase domain image.

23. The system of claim 22 wherein, in identifying the at least one of the electrode center and electrode contact locations of the DBS electrode, the computer is further programmed to:
   generate a simulated orientation-dependent field inhomogeneity ($B_0$) map from a software model of the DBS electrode and based on the estimated orientation of the DBS electrode; and
   compute a correlation between the $B_0$ map and the phase domain image to estimate the at least one of the electrode center and the electrode contact locations of the DBS electrode, with the at least one of the electrode center and the electrode contact locations of the DBS electrode being estimated by finding a translation value that maximizes the correlation between the $B_0$ map and the phase domain image.

24. The system of claim 23 wherein the computer is further programmed to perform a segmentation of the at least one of the magnitude domain image or phase domain image to provide an electrode region, with the first up-sampling and the estimation of the orientation of the DBS electrode being performed on the electrode region.

25. The system of claim 24 wherein the computer is further programmed to:
   adjust a cropping of the electrode region based on the estimated at least one of the electrode center and electrode contact locations of the DBS electrode to provide an adjusted electrode region;
   perform a second up-sampling on the at least one of the magnitude domain image and the phase domain image in the electrode region at a higher value than the first up-sampling;
   re-estimate the orientation of the DBS electrode within the adjusted electrode region;
   generate an adjusted simulated orientation-dependent field inhomogeneity ($B_0$) map from the software model of the DBS electrode and based on the re-estimated orientation of the DBS electrode; and
   compute an adjusted correlation between the adjusted $B_0$ map and the phase domain image to re-estimate the at least one of the electrode center and the electrode contact locations of the DBS electrode.

* * * * *